United States Patent
Krause et al.

(10) Patent No.: US 9,279,721 B2
(45) Date of Patent: Mar. 8, 2016

(54) GAS CELL FOR THE OPTICAL ANALYSIS OF GASES

(71) Applicant: Bruker Optik GmbH, Ettlingen (DE)

(72) Inventors: Sven Krause, Hamburg (DE); Yifei Wang, Hamburg (DE); Lars Schomann, Hamburg (DE); Gerhard Matz, Buchholz (DE); Roland Harig, Waldbronn (DE); Jens Eichmann, Hamburg (DE)

(73) Assignee: Bruker Optik GmbH, Ettlingen (DE)

( * ) Notice: Subject to any disclaimer, the term of this patent is extended or adjusted under 35 U.S.C. 154(b) by 0 days.

(21) Appl. No.: 14/637,425

(22) Filed: Mar. 4, 2015

(65) Prior Publication Data

US 2015/0185075 A1  Jul. 2, 2015

Related U.S. Application Data

(63) Continuation of application No. 13/885,178, filed as application No. PCT/EP2011/070462 on Nov. 18, 2011, now abandoned.

(30) Foreign Application Priority Data

Nov. 19, 2010 (DE) .......................... 10 2010 051 928

(51) Int. Cl.
*G01N 1/10* (2006.01)
*G01J 3/02* (2006.01)
*G01N 21/03* (2006.01)
*G01N 21/11* (2006.01)

(52) U.S. Cl.
CPC ............... *G01J 3/0267* (2013.01); *G01J 3/021* (2013.01); *G01N 21/031* (2013.01); *G01N 21/11* (2013.01); *G01N 2201/02* (2013.01)

(58) Field of Classification Search
CPC ....................................................... G01J 3/0267
USPC ........................................................... 356/246
See application file for complete search history.

(56) References Cited

U.S. PATENT DOCUMENTS 6,486,474 B1 * 11/2002 Owen et al. ............... 250/339.02

* cited by examiner

*Primary Examiner* — Tarifur Chowdhury
*Assistant Examiner* — Omar Nixon
(74) *Attorney, Agent, or Firm* — Paul Vincent

(57) ABSTRACT

A measuring cell for a gas analysis spectrometer has an inner chamber for a sample gas to be analyzed and an inlet and an outlet which are connected thereto. A traversing optical path for a measuring beam is formed in the inner chamber. The measuring cell is tubular, the inlet and the outlet are arranged at opposite ends, and the inner chamber of the measuring cell has a cross-sectional shape that is monotonic over the length of the tube and which has an oval-shape at the start, which disappears toward the end. That special shape results in fast gas exchange and thus high dynamics, even with larger measuring cells, which have high sensitivity due to the long optical paths thereof. Two characteristics which until now appeared to be conflicting are thereby combined.

6 Claims, 6 Drawing Sheets

GAS CELL FOR THE OPTICAL ANALYSIS OF GASES

This application is a continuation of Ser. No. 13/885,178, filed Jul. 18, 2013 as the national stage of PCT/EP2011/070462, filed on Nov. 18, 2011 and claims Paris convention from DE 10 2010 051 928.6, filed Nov. 19, 2010, the entire disclosures of which are hereby incorporated by reference.

BACKGROUND OF THE INVENTION

The invention concerns a measuring cell for a gas analysis spectrometer with an inner chamber for a gas to be analyzed, an inlet and an outlet, wherein a traversing optical path for a measuring beam is formed in the inner chamber.

The optical analysis of gases is applied widely in various areas of technology. Special requirements are demanded by exhaust gas measurement applications for internal-combustion engines. Due to increasingly strict exhaust gas regulations, not only is a high level of sensitivity required to achieve a low detection threshold, but also a high time resolution to ensure a sufficiently good dynamic response of the measurement, in particular, with respect to non-stationary operating states of internal-combustion engines. This results in a conflict of objectives between detection sensitivity and the time resolution of the system. In such measuring cells for optical gas analysis devices, the detection sensitivity depends on the optical path length that the measuring beam travels through the gas to be analyzed in the measuring cell. This path length, in turn, depends on the inner chamber volume of the measuring cell and the guidance of the measuring beam. However, the time resolution that is decisive for the dynamic response directly depends on the time needed to replace the gas to be analyzed in the measuring cell. It is important that the gas is replaced in its entirety. Increasing the volume of the measuring cell therefore has the disadvantage that, while other parameters remain constant, the time required to completely replace the gas increases, causing the time resolution and therefore the dynamic response to decrease correspondingly.

Various approaches for increasing the quality of the measurement are known from prior art. In many measuring cells, attempts are made to increase the detection sensitivity for a constant cell volume by optimizing the optical path. U.S. Pat. No. 5,440,143 A1 describes attaching a special mirror system onto an otherwise standard measuring cell with a square cross-section, which produces a multiply folded and therefore extended optical path for the measuring beam. Disposing multiple measuring cells one behind the other so that the measuring beam is first guided through a first measuring cell and then through another, is known from US 2007/0182965 AI. A universal measuring cell for adapting the length of the optical path is known from JP 10/062335 A, wherein the cell is constituted as two telescopic partial bodies.

An alternative approach has tried to influence the flow of sample gas within the measuring cell (DE 103 18 786 A). In such a measuring cell, however, relatively large "dead zones" are formed, which increase the exchange time and worsen the dynamic response. As FIG. 7 schematically shows, in a measuring cell (9) according to prior art, swirling (91) of sample gas in the measuring cell causes formation of dead zones in which molecules of the sample gas can dwell for a comparatively long time, preventing fast exchange. As the concentration of the supplied sample gas (90) changes, the previous concentration is still partly present so that the new concentration value can only be correctly determined once the gas in the dead zones has also been exchanged.

The resulting time delay causes carryover (concentration carryover), which in turn results in a long response time of the measuring cell and therefore of the entire measuring system.

The object of the invention is to create an improved measuring cell with a better dynamic response.

SUMMARY OF THE INVENTION

The inventive solution is a measuring cell with the characteristics of the independent claim. Advantageous embodiments are the subject of the dependent claims.

In a measuring cell for a gas analysis spectrometer with an inner chamber for a gas to be analyzed (sample gas) and an inlet and an outlet connected to it, an optical path traversing the inner chamber is formed for a measuring beam, wherein according to the invention, the measuring cell is constituted as a tube with the inlet and the outlet at opposite ends, and its inner chamber has a cross-sectional shape, which extends monotonically over the length of the tube, with an ovality at the start, which disappears toward the end.

Some of the concepts and terms used are explained below:

Inlet describes a facility through which sample gas can flow into the inner chamber of the measuring cell. Correspondingly, outlet describes a facility through which it flows out.

The beginning of the measuring cell describes the region where the inlet is positioned. Correspondingly, the end of the region is that which leads to the outlet.

Monotonic means a change that occurs in one direction only. An ovality that decreases monotonically along the length of the tube therefore means that at no point does the ovality increase along the length of the tube, not even intermittently.

The inventive measuring cell has a shape that is optimally adapted to the formation of a vortex at the inlet of the sample gas and the transformation of the vortex as it moves toward the outlet and in such a way that the flow of gas that moves from the inlet to the outlet fills the entire cell volume along a direct path. The emphasis here is on a direct path, i.e. secondary curls or other fluidic figures do not have to be formed to exchange the gas in remote zones (dead zones). Indeed, the inventive shape avoids the existence of such dead zones, resulting in particularly fast gas exchange due to the exchange along a direct path.

The invention has recognized that the dynamic response of the measuring cell can be improved not only with a particularly small size of the cell volume but, in contrast to previous attempts in prior art, also with a larger size of measuring cell having a special shape. This special shape is provided by the ovality on the inlet side, which disappears toward the outlet. As has already been mentioned, this special shape allows a particularly fast exchange of gas and produces the desired improvement in the dynamic response. This invention therefore no longer relies on an especially small size of measuring cell, enabling the measuring cell to be larger and therefore more robust. This lengthens the optical path for the measuring beam and these good optical conditions improve detectability of the measuring cell. The invention therefore achieves a combination of advantages with respect to improved dynamic response and improved detectability. It achieves this in a surprisingly simple way, namely solely by ingenious shaping of the measuring cell. There is no example of this in prior art.

To reliably achieve favorable vortex formation even as the sample gas flows in, the inlets are preferably disposed in the tube casing. Disposing them thereby in the region of the start of the tube has the advantage, compared to positioning on the start end face, that reliable and flow-advantageous main vortex formation can be achieved. This particularly applies when the inlets are disposed diametrically opposite each other, and offset with respect to the central axis of the tube shape. This not only applies if two inlets are provided but also if more than two inlets are provided: in this case, they should be disposed in such a way that the sample gas initially flows into the tube tangentially. With this configuration, the inflowing sample gas can be induced to swirl. This results in stabilization of the flow and ensures the desired penetration of the entire inner chamber volume with the main vortex.

The outlets for the exiting sample gas are preferably constituted with an axial component. This is understood to mean that the outlets have an angle of maximum 30° with respect to the tube axis. Disposing them on the casing allows the mirror for the measuring beam to be disposed in the center. In this way, the end region can be optimally used for generating the optical path for the measuring beam. Furthermore, this outlet configuration has the advantage that unimpeded exit of the gas can be achieved due to the considerable tangential component. The outlets are preferably tapered. This is understood to mean that at their start, i.e. in the region of their entry, they have the largest cross-section, which successively tapers the further it is from the inner chamber. It has been shown that a particularly good discharge characteristic from the inner chamber into the outlet of the sample gas can be achieved in this way, particularly with respect to the paucity or absence of reflections and the vortex or antivortex caused by them.

Preferably, the ovality in the region of the outlet disappears completely. This is not absolutely necessary, a slight ovality (compared with the inlet) can remain. Preferably, the shape of the tube of the measuring cell in the region of the outlet is circular. Advantageously, it is already circular at some distance (up to ⅓ of the total length of the tube) from the position where the outlet is disposed. In this connection, the cross-sections preferably have substantially equal surface areas despite being different in shape, wherein by "substantially" a deviation of no more than 15%, preferably 10% is understood.

In most cases, the outlet will be disposed in the end region of the tube. However, this is not absolutely necessary. Therefore, an additional element can be provided in addition to the tube, which has a cross-sectional shape that is inverse with respect to the tube. It is disposed in such a way that the non-oval side of the measuring body (i.e. its end) is connected to the correspondingly shaped beginning of the additional element, and the additional element changes to become oval along the length of the tube. This intermediate element therefore provides a sort of continuation of the original measuring length. This is especially suitable for the detection of sample gases in especially low concentrations.

The invention is explained below using the included drawing, which shows an advantageous embodiment.

The drawings show:

DESCRIPTION OF THE PREFERRED EMBODIMENT

Figure 1:
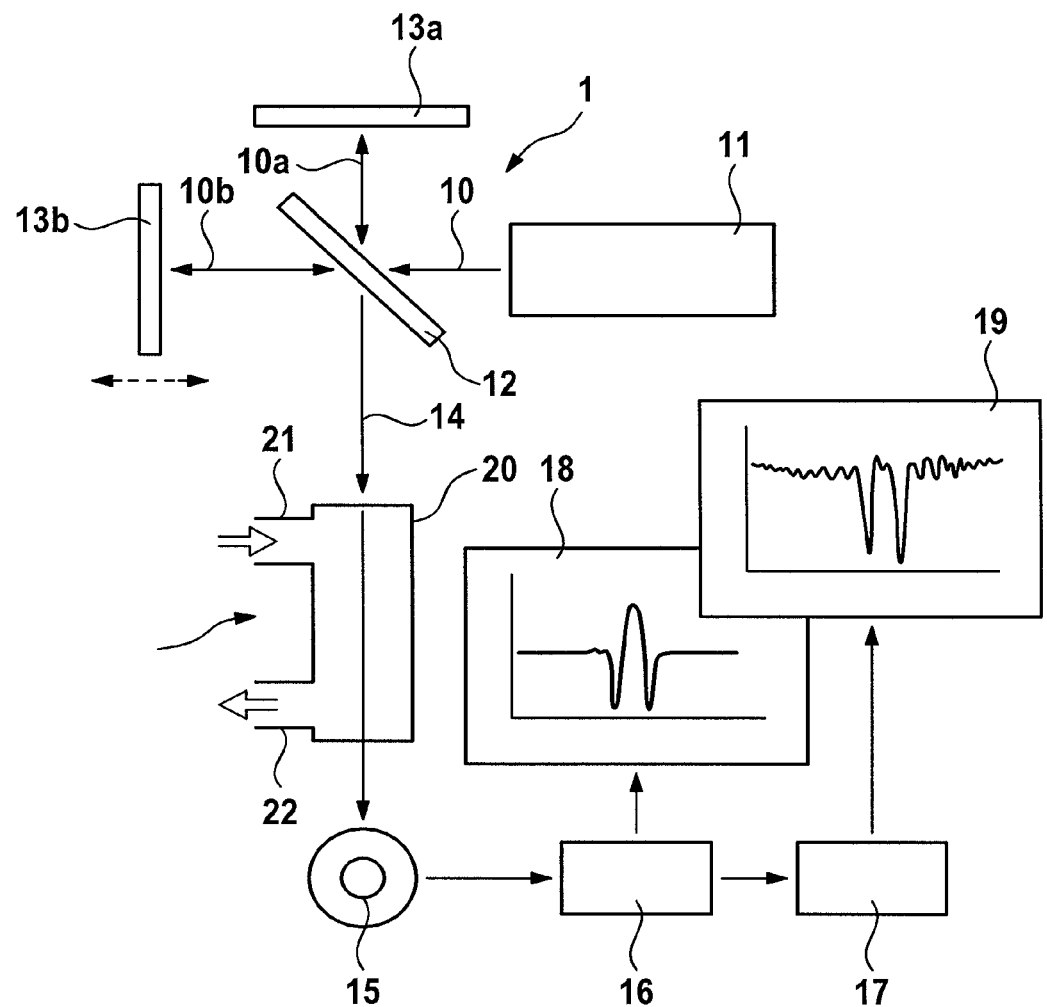
FIG. 1 A schematic representation of a measuring device with an inventive gas cell.
Figure 2:
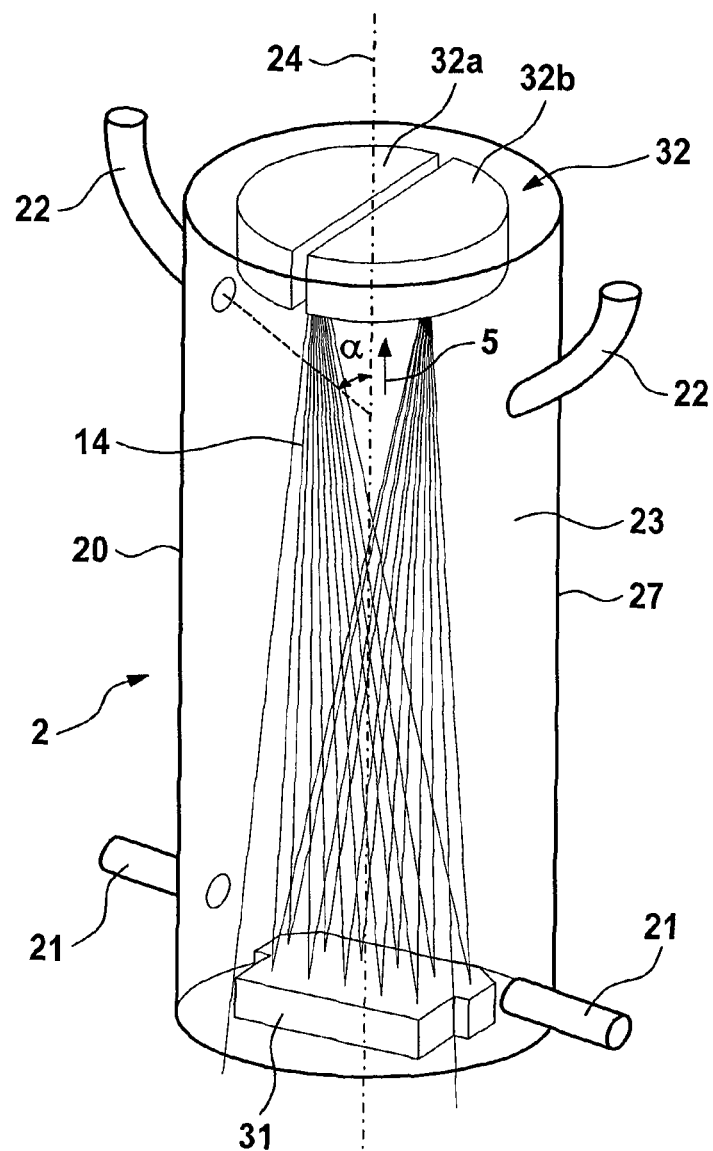
FIG. 2 A representation of the gas cell showing the beam path.

The invention is explained using the example of an FTIR spectrometer. FTIR stands for Fourier transform infrared spectroscopy. Such devices are known from prior art and will therefore be only briefly explained with reference to FIG. 1.

An infrared light beam 10 (IR beam) from a source 11 for infrared radiation is focused onto an obliquely disposed beam splitter 12 of an interferometer, which is collectively designated by reference numeral 1. The IR beam 10 is divided into two components 10a and 10b, of which component 10a is reflected by the beam splitter 12 to a fixed mirror 13a, and component 10b is allowed to pass through to a movable mirror 13b, whose distance from the beam splitter 12 can be altered (symbolized by the dashed double-headed arrow in FIG. 1). The partial beams 10a, 10b reflected back by the mirrors 13a, 13b, interfere at beam splitter 12 and are together radiated as IR measuring beam 14 into a gas cell 2.

Figure 7:
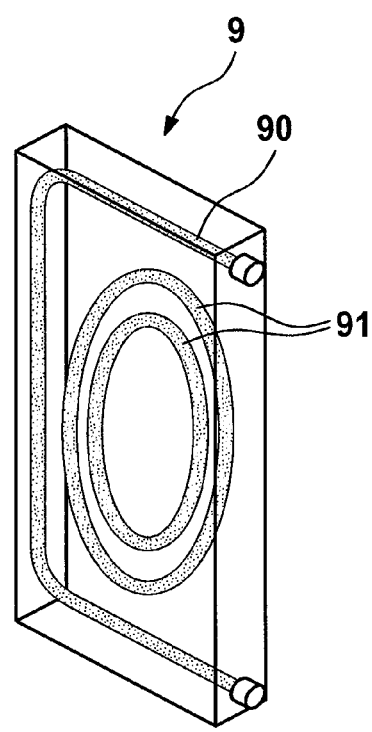
FIG. 7 A conventional gas cell.

The gas cell 2 is the actual measuring cell. Conventionally, it is constituted in the shape of a cell or vessel (cf. FIG. 7). It has an elongated basic body 20 with an inlet 21 at one end and an outlet 22 at the other end. The gas to be analyzed flows through the inlet 21 into the basic body, fills the latter and flows out again through the outlet 22. While the gas dwells in the basic body 20, the gas is irradiated by the measuring beam 14. Depending on the composition and concentration of the gas in the gas cell 2, different components of the spectrum of the measuring beam 14 will be absorbed and the remaining component that is allowed to pass through (transmitted) is projected onto a detector 15.

Detector 15 is an MCT semiconductor detector, which converts the change in photon intensity into an electrical quantity. However, a photodiode, a bolometer or the like can also be used. The signal measured by detector 15 is guided to an analog/digital converter 16. The interferogram 18 can be displayed on a suitable display device. Then, what is now a digital signal is processed by a transformation element 17 by means of fast Fourier transform (FFT). It is constituted to generate a spectral representation 19 from the interferogram provided by the analog/digital converter 16 in a known way and to display it.

The functional and structural configuration of gas cell 2 is shown in FIGS. 2 to 6. As FIG. 2 most clearly shows, the gas cell has an elongated, round hollow basic body 20 with a double-entry inlet 21 at one end and a double-entry outlet 22 at its other end. The basic body has a cavity 23, which is delimited by a casing 27. According to a core element of the invention, the cross-section of the cavity 23 in the basic body 20 is not constant but changes continually from inlet 21 to outlet 22. According to the invention, the shape of the cross-section of the cavity 23 has been chosen such that the cross-section is oval at inlet 21 and this ovality is increasingly reduced toward outlet 22, until it practically disappears completely in the region of outlet 22, i.e. there, the cross-section is practically circular. This permits use of a round mirror 32 in the outlet region to reflect the measuring beam 14 and a polygonal mirror 31 in the region of the inlet cross-section. The mirrors 31, 32 have the same radius of curvature.

Figure 3:
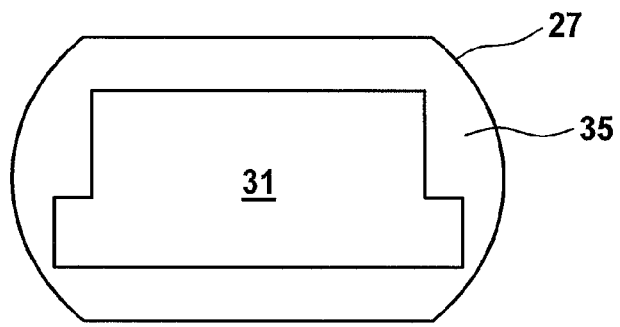
FIG. 3 A view from above onto the gas cell without its inlet and outlet.

As best illustrated in the plan view of FIG. 3, the polygonal mirror 31 has an elongated shape which seats within an inner periphery of the casing 27 proximate the inlet region at which the casing 27 exhibits its oval cross section. The shapes of the polygonal mirror 31 and the casing 27 are therefore matched to another in the oval region of the casing 27. The oval casing 27 therefore has a substantially smaller cross section in the inlet region than that of a casing 27 having a circular cross section of sufficient size to accommodate the elongated shape of the polygonal mirror 31. This, in turn, leads to a casing 27 whose overall volume is reduced compared to a circularly cylindrical casing of sufficient diameter to accommodate the elongated shape of polygonal mirror 31. The reduced volume of the oval, tapering casing 27 leads to an associated reduction in the dwell time of the gas sample within the measuring cell. Decreasing the volume of the measuring cell therefore has the advantage that, while other parameters remain constant, the time required to completely replace the gas decreases, causing the time resolution and therefore the dynamic response to improve correspondingly.

The inlets 21 are disposed on the basic body 20, diametrically opposite along the longer axis of the oval, with a small offset in opposite directions (less than one tenth of the size of the width of the basic body 20 in this region) relative to the center axis 24 of the basic body 20. In this way, it is ensured that the sample gas flowing in quickly fills the oval-shaped cross-section. An intended asymmetry is achieved by this offset with which the flow in the cavity 23 takes a preferred direction so that a defined vortex can form, which ensures fast mixture at the beginning and during continued flow of the sample gas toward outlet 22. Because of the tapered cross-sectional shape, the vortex along the path to the outlet 22 gradually turns into a circular vortex and its peripheral speed slowly decreases. At the outlet end, the outlets are disposed diametrically opposite and oriented in such a way that they are tangential to the direction of flow (symbolized by arrow 5) from inlet 21 to outlet 22 and form an angle α of approx. 25° with respect to the center axis 24. In this way, the sample gas can exit the gas cell 2 via the outlets 22 in a way that is favorable to the flow.

Figures 4, 5:
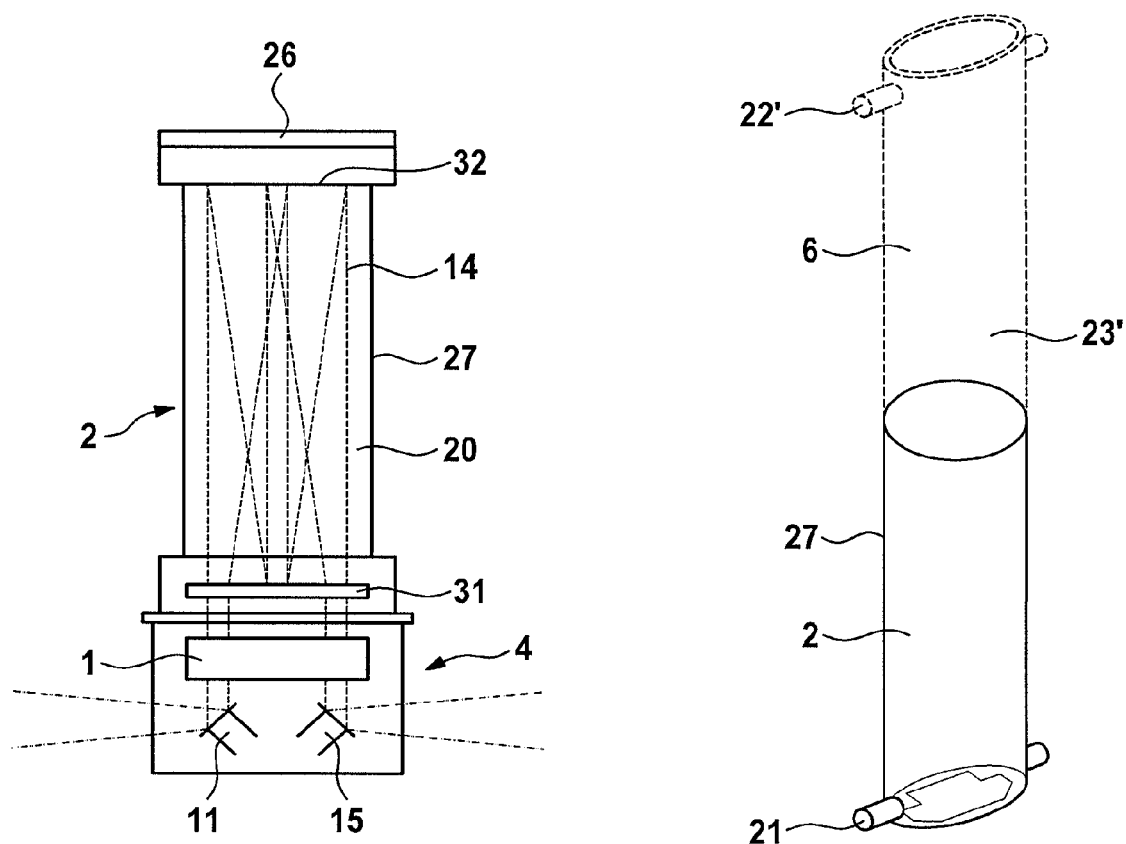
FIG. 4 A sectional view of the gas cell.
FIG. 5 An alternative embodiment of the gas cell.
Figure 6:
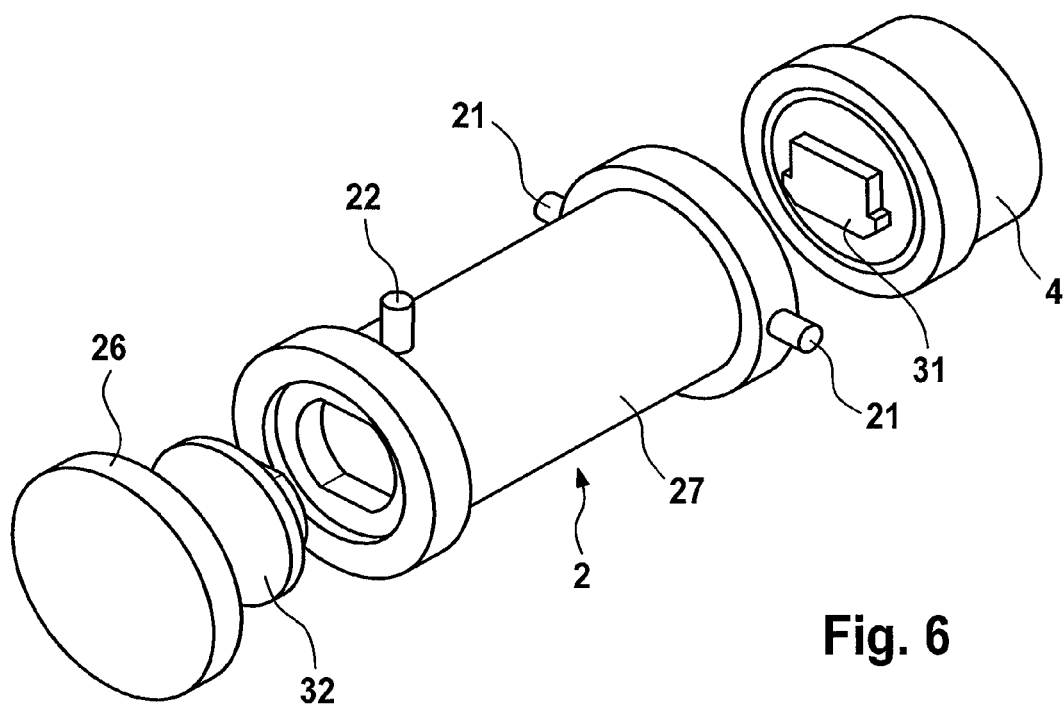
FIG. 6 An exploded view of the gas cell according to FIG. 2.

The beam guidance with the IR source 11 and the detector 15 und the installation location with reference to the gas cell 2 are shown in FIG. 4. The measuring cell 2 represented in the embodiment is 16 cm long and has a 7.5-cm diameter. A floor-sided pot 4 is provided beneath the actual gas cell 2, in which the IR source 11, the detector 15, and the interferometer 1 are disposed. The IR source and detector can also be disposed externally, in which case corresponding access openings for the inflow and outflow (represented by a dashed line) would have to be provided. They radiate through openings located at the edge of the polygonal mirror 31 (see reference FIG. 35 in FIG. 3). Taking into consideration this surface intended for the beam entry and exit, the polygonal mirror 31 forms an envelope that is elliptical. The gas cell 2 is closed at its top end by a cover 26. Further, the round mirror 32 is disposed on the inside of the cover 26 so that it faces the polygonal mirror 31. The round mirror 32 is configured as a double mirror comprising two parallel concave mirrors 32a, 32b. Their radius of curvature is identical and dimensioned such that their focal points are located on the surface of the opposite mirror 31. Mirror 31 is also concave, wherein its focal point is aimed exactly onto the center of the two concave mirrors 32a, b. This results in a multiply reflected, fanned out light path for the measuring beam 14, which forms a stationary beam pattern in the two concave mirrors 32a, b, and a beam pattern on the polygonal mirror 31 that moves slightly each time it reflects back and forth. In this way, both mirrors 31, 32 are illuminated fully for the measurement. All the input light is reflected from one mirror 31, 32 to the other 32, 31, so that there is practically no loss. The fanning out with multiple reflection produces a light path that is a multiple of the actual overall length of the gas cell 2 (see FIGS. 2 and 4).

Several advantages are achieved in this way. On the one hand, sample gas flowing in at inlet 21 is immediately caught by measuring beam 14, which results in a very fast response time. The sample gas is measured before it even has time to mix with the old gas still present in gas cell 2. As a result, changes to the composition and/or concentration in the sample gas are visible practically immediately. The invention has also recognized that the claimed cross-sectional transition shape not only provides advantages in terms of minimizing the internal volume of the gas cell 2 but is also provides favorable conditions for flow. When the sample gas flows in, a vortex is formed, which more or less fills the entire cross-section in the inlet area, and changes shape along its path to the outlet such that it acquires an increasingly circular cross-section. The invention takes advantage of the behavior of the measuring gas vortex by adapting the cross-sectional shape of the gas cell precisely to this change in shape, thus having a cross-section along the entire length of the gas cell that is entirely filled by the flow. This effectively reduces the "dead zones," which are critical to the response and precision. Because the gas exchange in the gas cell is faster than the measurement of an interferogram, a maximum dynamic response is achieved.

The long light path results in a high level of sensitivity. The light fan produced between the polygonal mirror 31 and the circular mirror 32 is optimally adapted to the cross-sectional shape of the inner chamber. This results in practically the entire inner chamber being irradiated and, because of the complete filling with the flow described above, quickly being filled with the entering sample gas (without formation of the disturbing dead zones known from prior art). The wide fanning in conjunction with the flow pattern produced by the special shape ensures a fast response. In this way, the inventive gas cell can provide two essential advantages at once.

To further increase the sensitivity while maintaining the advantageous dynamic properties, an alternative embodiment is possible. It has an additional element 6, which is directly connected to the gas cell 2. In this case, the cover 26 of the gas cell 2 is eliminated so that, together with the additional element, a large uniform cavity 23' is produced. The shape of the cavity in the additional element 6 is inverse, i.e. circular where it forms a connection with casing 27 of the gas cell 2 and oval at the outside end. The additional element 6 is preferably constructed identically and connected to the coverless gas cell 2 in a "back-to-back" configuration. Inlet 21 is located at the base of gas cell 2 and inlet 22' is located at the other end at the additional element 6. With this configuration, the sensitivity can be almost doubled, wherein the advantageous shape of the gas cell 2 is retained due to the mirrored shape of the cavity of the additional element 6.

Figure 8:
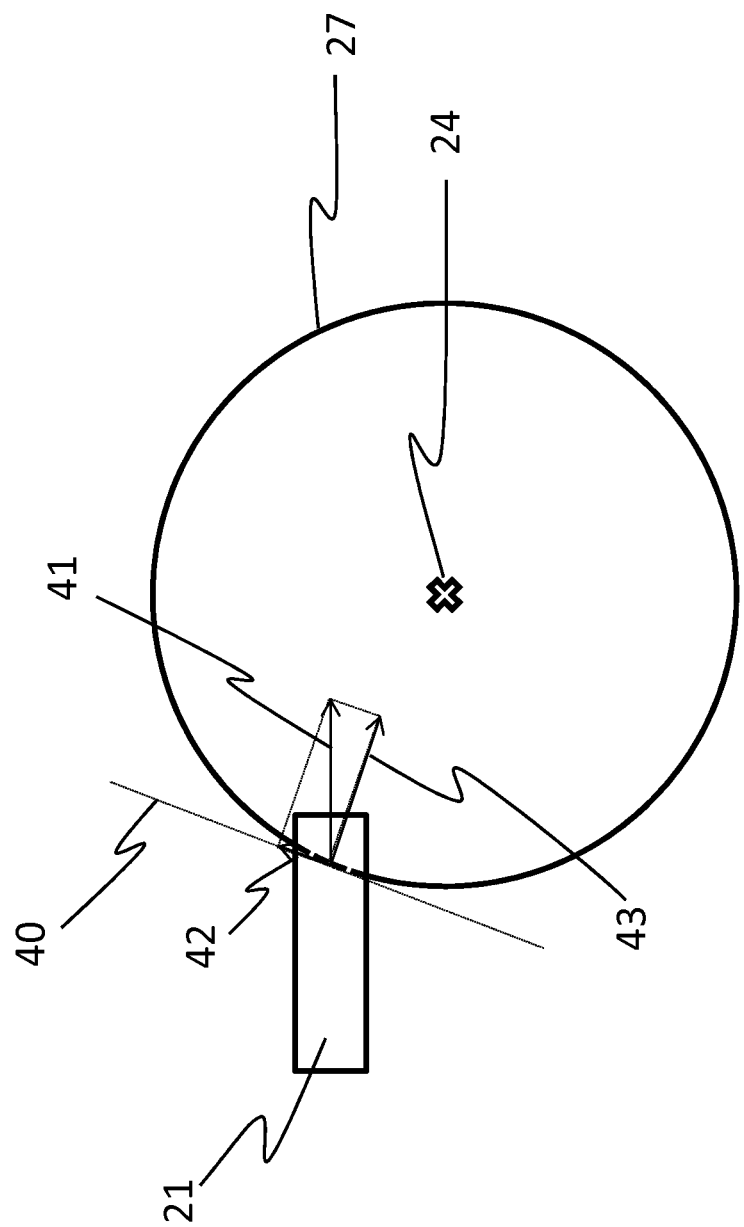
FIG. 8 A bottom or top view of a gas cell casing.

FIG. 8 shows a schematic view of the gas cell casing 27 from a bottom or top perspective with at least one inlet 21 and center axis 24. The inlet is tilted with respect to the tangent 40 of the rounded structure of the gas cell 27 at the position where the inlet 21 penetrates the gas cell casing 27. Accordingly, the direction of alignment of the inlet 41 has a tangential vector component 42 and a vector component 43 perpendicular to the tangent 40. This tangential component 42 of the inlet allows the gas to be inserted more efficiently into the gas cell.

Figure 9:
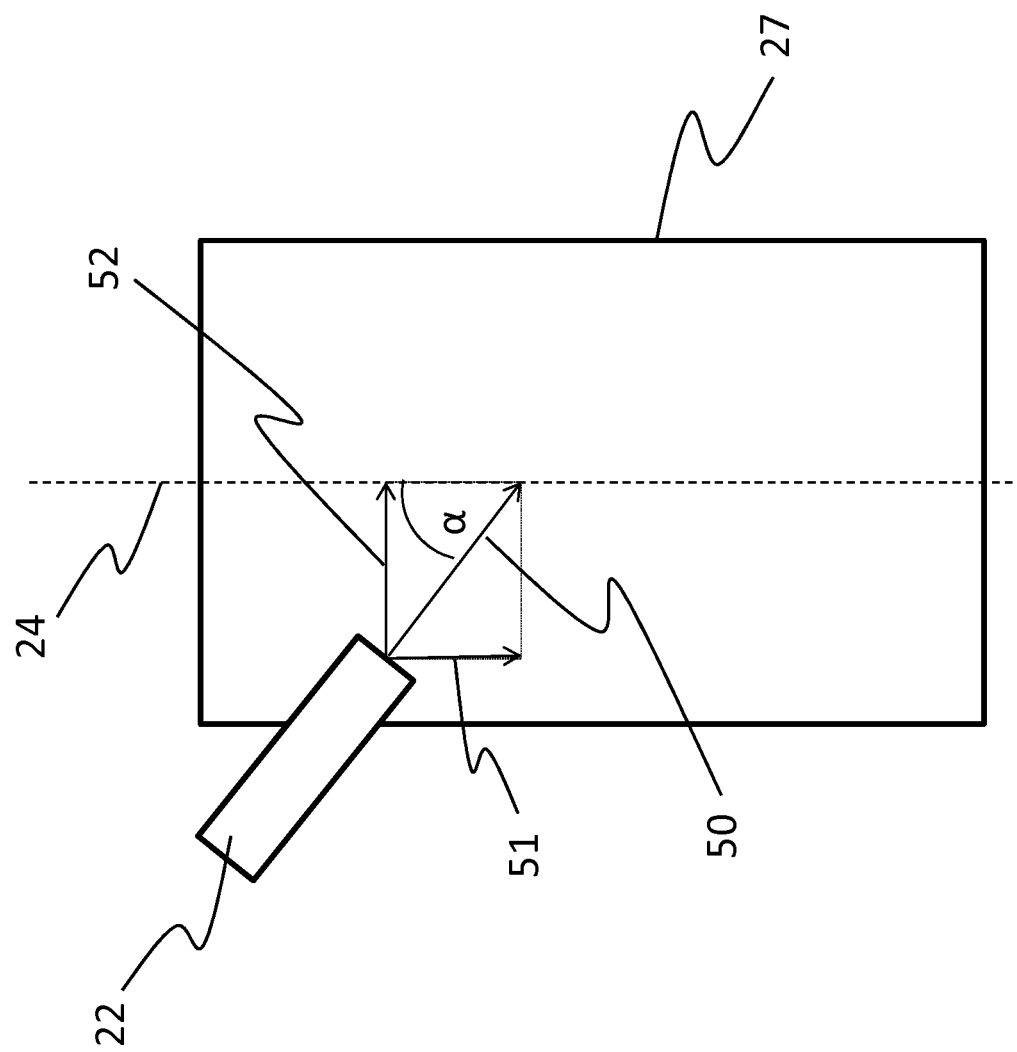
FIG. 9 A side view of the gas cell casing.

FIG. 9 schematically shows the gas cell casing 27 in a side view with at least one outlet 22 and center axis 24. The outlet is tilted with respect to the center axis 24 of the gas cell 27 at the position where the outlet 22 penetrates the gas cell casing 27. Accordingly, the direction of alignment of the outlet 50 has an axial vector component 51 and a vector component 52 perpendicular to the axis 24. This axial component 51 of the outlet allows the gas to be extracted more efficiently from the gas cell.

We claim:

1. A flow-through measuring cell for a gas analysis spectrometer, the measuring cell comprising:
    a casing having a tubular inner chamber for a sample gas to be analyzed, said casing having a first end, a second end and a center axis;
    an inlet mounted on said casing proximate said first end, said inlet having a tangential component;
    an outlet mounted on said casing proximate said second end, wherein the sample gas passes from said inlet, through said tubular inner chamber and into said outlet, said casing having a substantially oval, non-circular cross-sectional shape proximate said inlet, which decreases monotonically along a length thereof and substantially vanishes proximate said outlet;
    a first concave mirror having an upper reflective surface, said first concave mirror being disposed between said inlet and said first end of said casing, said first concave mirror having an elongated shape which seats within and is matched to said oval cross-sectional shape of said casing, wherein the sample gas passes from said inlet directly into said casing at an axial location along said casing which is above said upper reflective surface of said first concave mirror; and
    a second concave mirror disposed between said outlet and said second end of said casing, said first and said second mirrors thereby inducing a multiply reflected, fanned out optical path for a measuring beam in said casing, wherein said tangential component of said inlet and said cross-sectional shape of said casing are disposed, structured and dimensioned to generate a defined vortex of sample gas flow within said casing, said vortex gradually turning into an increasingly circular vortex with a slowly decreasing peripheral speed as the sample gas passes from said inlet to said outlet.

2. The measuring cell of claim 1, wherein an axial component of said outlet is disposed in such a way that said outlet forms an angle of no more than 30° with a center axis of the measuring cell.

3. The measuring cell of claim 1, wherein said outlet has a cross-section that is tapered towards an outside.

4. The measuring cell of claim 1, wherein said casing has a substantially circular cross section proximate said outlet.

5. The measuring cell of claim 1, wherein said cross sectional shape of said casing at said inlet and said outlet differ but have a substantially same surface area.

6. The measuring cell of claim 1, further comprising an additional element which is connected to an outlet end and has a cross-section progression, which is inverse with respect to said casing.

* * * * *